US00PP13279P2

(12) United States Plant Patent
Khanuja et al.

(10) Patent No.: US PP13,279 P2
(45) Date of Patent: Nov. 26, 2002

(54) MINT PLANT NAMED 'SAKSHAM'

(75) Inventors: Suman Preet Singh Khanuja, Lucknow (IN); Sushil Kumar, Lucknow (IN); Ajit Kumar Shasany, Lucknow (IN); Sunita Dhawan, Lucknow (IN); Mahendra Pandurang Darokar, Lucknow (IN); Ali Arif Naqvi, Lucknow (IN); Om Parkash Dhawan, Lucknow (IN); Anil Kumar Singh, Lucknow (IN); Nirmal Kumar Patra, Lucknow (IN); Janak Raj Bahl, Lucknow (IN); Ram Prakash Bansal, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/721,777

(22) Filed: Nov. 27, 2000

(51) Int. Cl.[7] ..... A01H 5/00
(52) U.S. Cl. ..... Plt./259
(58) Field of Search ..... Plt./259, 258

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

This invention relates to a new and distinct mint plant of *Mentha arvensis* 'Saksham', developed through tissue culture, possessing the following combination of characters namely producing higher amount of menthol with high essential oil yield as well as herbage yield; possessing better growth and vegetative growth with high regenerability; has distinct molecular profile by random amplified polymorphic DNA (RAPD); retains the characteristics of tolerance to leaf spot, rust and powdery mildew as in the parent variety 'Himalaya'; has light greenish leaves, pinkish white flowers like the parent plant 'Himalaya', this new plant is able to produce higher herbage, oil and menthol yield per unit area as compared to other existing improved varieties.

1 Drawing Sheet

BOTANICAL/COMMERCIAL CLASSIFICATION

Figure 1:
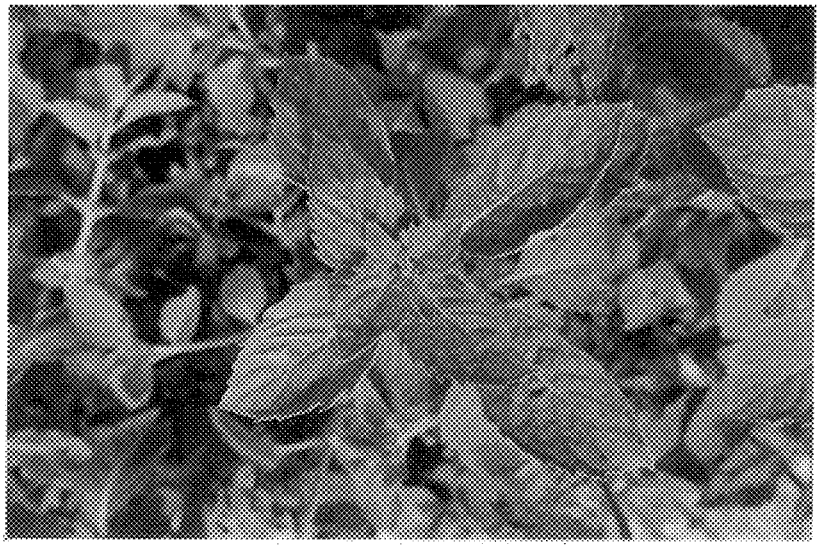

*Mentha arvensis* Linn./Japanese Mint Plant.

VARIETAL DENOMINATION cv. Saksham.

FIELD OF INVENTION

The present invention is related to the development of a novel high menthol producing plant obtained through a unique method of screening of the somaclones in poison agar medium containing toxic level of menthol. The selected plant is tolerant to high concentration of menthol in cultures and hence possesses property of accumulating more menthol per unit leaf mass due to shifted feed back inhibition by menthol as end product. The essential oil yield from the said plant is high coupled with the property of being rich in menthol. This plant is unique and clearly distinct from all other existing varieties of *Mentha arvensis* L. The new variety was initially designated GRB 30. The new variety has been named as 'Saksham' (meaning capable) which can be propagated vegetatively through suckers for commercial cultivation.

BACKGROUND OF THE INVENTION

*Mentha arvensis* Linn. Var *piperescens*. Holmes (menthol or Japanese mint) is a highly valued industrial crop due to menthol, which is purified by crystallisation through freezing from its essential oil. In the varietal improvement programs, the genetic alternations leading to enhancement in the menthol content in the essential oil and improving other adaptive characters determining the yield and quality of essential oil are most desirable. Menthol is produced from geranyl pyrophosphate through a series of intermediates and the level of production of the high value product menthol is controlled through feed back inhibition of the accumulated end product (which is menthol here). It appears that beyond a certain limit of menthol during the biosynthesis the enzymes involved are inhibited by the end product preventing further forward reaction. Also, monoterpenes are known to be cytotoxic to plant tissues, by inhibiting respiration and photosynthesis by drastically affecting the mitochondria, golgi bodies etc and decreasing cell membrane permeability (Brown J T, Hegarty P K, Charlwood B V, 1987. The toxicity of monoterpenes to plant cell cultures. Plant Science 48: 195–201). Monoterpenes are either sequestered in the plants in specialized structures like glandular hairs in Pelargonium (Brown J T, Charlwood B V, 1986, Differentiation and monoterpene biosynthesis in plant cell cultures. In Morris P, Scragg A, Stafford A and Fowler M, ed Secondary Metabolism in Plant Cell Cultures. Cambridge University Press, Cambridge, 1986, p. 68), trichomes in Mentha or stored in the form of non-toxic glycoside derivatives in vacuoles e.g. Rosa spp. The end product toxicity in such cases can be related to the feed back inhibition to regulate the extent of monoterpenes that can be accumulated within tolerance limits. Menthol, the major component of the essential oil, which is considered to be cytotoxic to the plant, could be so due to toxicity mechanism related to the end product. To this corollary, the level of menthol accumulated in leaf tissues may be linked to the level of menthol tolerance. Uncoupling of these two factors may thus deregulate the rate-limiting step in the production of menthol. With this rationale, the applicants attempted to screen the somaclones available with us and tested to select clones tolerant to high level of menthol with the possibility of selecting high menthol yielding clones. It was assumed that through certain alternate mechanism cellular components may escape toxicity and damaging effect of higher menthol in the tissues by circumventing feed back inhibition level. Such a condition may lead to more menthol accumulation in the trichomes of the regenerated menthol tolerant plant which indeed happened and the applicants could screen out a stable high menthol containing clone showing enhanced tolerance to menthol in vitro.

OBJECTS OF THE INVENTION

The main object of the invention is to develop a new and distinct plant through tissue culture, said plant being capable of producing higher menthol with high essential oil yield as well as herbage yield.

Another object of the invention is to develop a new plant which possesses better vegetative growth with high regenerability.

Still another object of the invention is to retain certain original characters of the parent plant.

SUMMARY OF THE INVENTION

This invention provides a new and distinct mint plant of *Mentha arvensis* 'Saksham', developed through tissue culture, possessing the following combination of characters namely producing higher amount of menthol with high essential oil yield as well as herbage yield; possesses better growth and vegetative growth with high regenerability; has distinct molecular profile by random amplified polymorphic DNA (RAPD); retains the characteristics of tolerance to leaf spot, rust and powdery mildew as in the parent variety 'Himalaya'; and has light greenish leaves, pinkish white flowers like the parent plant 'Himalaya'. This new plant is able to produce higher herbage, oil and menthol yield per unit area as compared to other existing improved varieties.

The new plant 'Saksham' of the present invention was produced at the Central Institute of Medicinal and Aromatic Plants field station Pant Nagar, Lucknow, India.

The new variety of the present invention commonly produces a significant number of suckers, and has been asexually reproduced at the same location in India by division. The 'Saksham' plant is firmly fixed in its characteristics and has been found to reproduce true to type through successive generations of such asexual reproduction.

DETAILED DESCRIPTION

The invention provides a new and distinct mint plant of *Mentha arvensis* 'Saksham', developed through tissue culture, possessing the following combination of characters:

a) Produces higher amount of menthol (83% of oil) with high essential oil yield (0.8 to 1.0%) as well as herbage yield (at least 1.83 Q per 100 $m^2$),
b) Possesses better growth and vegetative growth with high regenerability covering at least 77 cm canopy area and a height of at least 72 cm in a maximum of 100 days,
c) Has a distinct molecular profile by random amplified polymorphic DNA (RAPD) using 20 random primers distinguishing the plant from the other existing varieties,
d) Retains characteristics of tolerance to leaf spot, rust and powdery mildew as in the parent variety 'Himalaya'.
e) Has light greenish leaves (138B), pinkish white flowers (56C) like the parent plant 'Himalaya', and
f) Produces higher herbage, oil and menthol yield per unit area as compared to other existing improved varieties.

The applicants used the plant 'Himalaya' (U.S. Plant Pat. No. 10,935), an elite mint genotype for large scale screening of in vitro raised clones (Khanuja S P S, Shasany A K, Dhawan S, Sushil Kumar, 1998, Rapid procedure for isolating somaclones of altered genotypes in *Mentha arvensis*. J medicinal and Aromatic Plant Sciences 20:359–361) to select clones tolerant to high menthol concentration in the medium (An efficient in vitro selection procedure for large scale screening of mint clones to isolate high menthol genotypes. Khanuja et al, Procedure patent pending, 1999).

While testing the tolerance of in vitro regenerates in presence of menthol in the MS based medium (Murashige T and Skoog F, 1962, A revised medium for rapid growth and bioassay with tobacco tissue cultures; *Physiol. Planta.* 15 473–497), the initial toxicity symptoms were first observed at the menthol concentration of 40 $\mu g\ ml^{-1}$ menthol after 7 days. The immediate symptoms of menthol toxicity were observed at menthol concentration of 70 $\mu g\ ml^{-1}$ within 24 hours. Here it was immediate chlorophyll loss and irreversible wilting of the shoots, non-rescuable even by culturing these regenerates in normal medium without menthol. Lowest survival was detected at a concentration of 70 $\mu g\ ml^{-1}$, where only 1% shoots could survive. Since at 50 $\mu g\ ml^{-1}$ concentration of menthol, also typical symptoms of toxicity were observed, a stepwise selection pressure of menthol concentration in the medium was employed in the large scale screening experiment, to enrich for the potentially tolerant shoots which presumably resort to the adaptive response by tolerating this medium level of menthol concentration through the induction of genes required for the tolerance, before transfer to the higher level. Ultimately 36, clones were selected for tolerance at 70 $\mu g\ ml^{-1}$ menthol by screening about 2950 clones. These were transferred to field for evaluation in a plant test area at Lucknow, India. Out of all the clones selected and grown outdoors in the field, one clone GRB-30 was observed to be growing better with high essential oil yield and higher menthol content. Further, on retesting in vitro, this clone could tolerate even 80 $\mu g\ ml^{-1}$ menthol in the culture medium. Considering the stability of the multiplied clone for menthol tolerance and increased menthol production it was logically assumed that the mother cells in vitro might have undergone some genetic changes to give rise to these variant (clones) and as a consequence of selection pressure of menthol, ultimately got selected as menthol tolerant genotypes with much higher tolerance level than the control plant 'Himalaya'. The selected clone named 'Saksha' (meaning capable) demonstrated significantly high menthol production per unit biomass and hence represents the superior genotype with the capability for large-scale commercial cultivation. The comparative field evaluation for two years 1998–1999 and 1999–2000 for growth and yield traits is given in Table 1, where the checks included parent variety 'Himalaya' and another superior genotype 'Kosi' (non-patented in the United States) in addition to a high menthol tolerant but low herbage yielding variety 'Kalka' (non-patented in the United States).

DESCRIPTION OF THE PHOTOGRAPHS

FIG. 1: represents top view of the branch.

Figure 2:
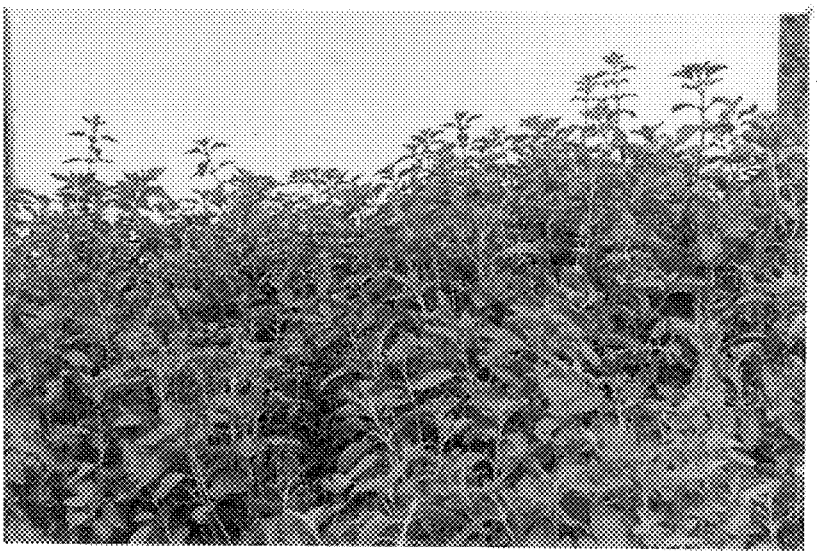

FIG. 2: represents 'Saksham' in the field.

Figure 3:
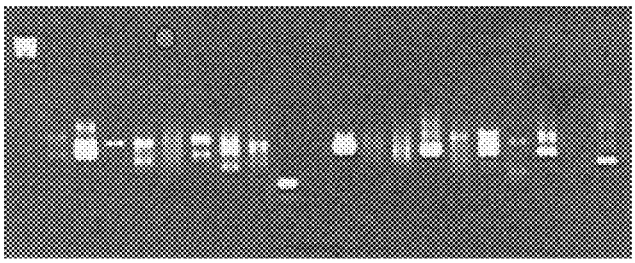

FIG. 3: represents RAPD profile with 20 OPT primers.

TABLE 1

Comparative growth and yield characteristics of plant of invention 'Saksham' in relation to the existing Japanese mint varieties (Average of field trials in the years 1998–1999 and 1999–2000).

| Property | 'Himalaya' | 'Kalka' | 'Kosi' | 'Saksham' |
|---|---|---|---|---|
| Plant height | 60.9 + 6.2 | 51.6 + 2.7 | 66.2 + 1.1 | 72 + 2.0 |
| Canopy (cm) | 62–70 | 40–60 | 65–72 | 77–86 |
| Leaf number | 40.2 + 4.2 | 38.0 + 2.0 | 50.4 + 3.8 | 45.0 + 0.5 |
| Branch length | 40.4 + 4.5 | 45 + 6.7 | 52.0 + 4.7 | 59.0 + 2.0 |
| Branch | 29.2 + 4.0 | 27.2 + 1.1 | 30.4 + 1.7 | 46.1 + 2.3 |
| Leaf length | 7.1 + 0.5 | 7.4 + 0.8 | 7.40 + 0.1 | 8.0 + 0.1 |
| Leaf breadth | 4.5 + 0.2 | 4.0 + 0.3 | 4.60 + 0.5 | 5.2 + 0.3 |
| Petiole length | 1.75 + 0.3 | 1.5 + 0.5 | 1.4 + 0.3 | 2.2 + 0.2 |
| Oil % | 0.7 | 0.8 | 0.8 | 0.9 |
| Menthol % | 80 | 82 | 74 | 85 |
| Herbage yield | 1.25 | 0.80 | 1.70 | 1.83 |
| Oil yield (Kg | 0.875 | 0.640 | 1.390 | 1.560 |
| Menthol yield | 0.700 | 0.525 | 1.056 | 1.295 |

As evident that 'Saksham' was the highest menthol yielder which surpassed all the check varieties. It produced 22.6% higher menthol over the best variety 'Kosi' in the yield trials and hence was named 'Saksham' meaning capable.

Taxonomic Description of the Mint Plant 'Saksham'

The description is based upon the observation during January of 'Saksham' growing outdoors 90 days after planting in test fields at Lucknow, India while using standard agronomic practices. The plants were harvested 110 days after planting.

1. Genus: Mentha.
2. Species: *arvensis* L.
3. Family: Lamiaceae.
4. Common name: Japanese mint/corn mint/menthol mint.
5. Plant height cm: Approximately 72.0+2.0.
6. Plant canopy cm: Approximately 77 to 86.
7. Growth habit: Erect sturdy main stem, profuse synchronous branching.
8. Stem: Round to quadrangular hard, woody, green (143C), faint purplish red pigmentation at the base (59B), 5 to 9 mm thick at $5^{th}$ internode.

Number of branches: Approximately 8 to 25.

Number of nodes:

*Main branch.*—Approximately 20 to 35.

*Upper branch* (*30 $^{th}$ node*).—Approximately 3 to 5.

*Middle branch* (*20 $^{th}$ node*).—Approximately 4 to 8.

*Lower branch* (*$10^{th}$ node*).—Approximately 4 to 8.

Range of Length of Internodes

Main branch (from lower to uppernodes in cm): Approximately 1.0 to 5.5.

9. Leaf:

*Color.*—Light green (138B) upper surface, Yellow green (139C) lower surface.

*Texture.*—Moderately thick and rigid.

*Surface.*—Hairy and rough.

*Shape.*—Generally elliptic.

*Margin.*—Moderately deep serration (approximately 15 to 50 in number).

*Tip.*—Acute.

*Base.*—Attenuate.

*Size.*—Moderately broad.

*Petiole length* (*cm*).—Approximately 2.2+0.0.

*Area.*—Approximately 15.6 $cm^2$ (Average of full branch).

*Length* (*cm*).—Approximately 8.0+0.10.

*Width* (*cm*).—Approximately 5.2+0.03.

*Fragrance.*—Possesses smell of menthol.

*Number of trichomes per leaf* (*Avg. trichomes× 1000*).—Approximately 1420.

*Trichome ratio* (*lower leaf /upper leaf*).—Approximately 3.41.

10. Leaf: stem ratio (w/w): Approximately 1.5.
11. Inflorescence: Raceme of axillary verticillasters. Total numbers of florets approximately 20 to 35.
12. Flowers: Arranged in whorls surrounding the stem at the base of lateral leaves.

*Shape.*—Tubular.

*Pedicel length* (*mm*).—Approximately 2.1 to 3.9.

*Pedicel.*—Yellow green (145C).

*Calyx diameter.*—1 mm, four fused.

*Calyx.*—Four, Yellow green (143C).

*Calyx texture.*—Rough.

*Corolla.*—Pinkish white, four, fused to a bell-shaped corolla tube (56D), 3 to 4 mm long.

*Corolla texture.*—Smooth.

*Arrangement.*—In whorls surrounding the stem at the base of lateral leaves.

*Length.*—Small and commonly approximately 3.8 mm when in full bloom.

*Anthers.*—Four, come out of the corolla tube.

*Stigma.*—Red-Purple Group 71C.

*Color of ovaries.*—Yellow-Green Group 151A.

*Time to flowering.*—April to May (approximately 60 to 70 days after planting first flowering is detected).

*Fruits/seeds.*—None observed to date.

13. Oil content in the fresh: Approximately 0.8 to 1.0. herb (%).
14. Oil quality:

*Menthol content* (%).—Approximately 82 to 87.

*Congealing point.*—Approximately 2 to 21° C.

15. Herbage (Shoot biomass Q/100 $m^2$): Approximately 1.83.

The color indications throughout are in accordance with The R.H.S. Colour Chart published by The Royal Horticultural Society, 80, Vincent Square, London, SWIP 2PE, 1995; which has internationally recognized and accepted.

The plant 'Saksham' in addition to producing more menthol in the essential oil comparatively yielded more essential oil per unit shoot biomass. The higher menthol yielding commercial variety of CIMAP 'Kalka' (CIMAP/HY-77) produced maximum 0.8% essential oil containing 82% menthol. But the variety yielded less biomass per unit are (0.8 Q per 100 $m^2$). Compared to this 'Saksham' produces maximum of 0.90% essential oil with 85% menthol and the plant yields more biomass per unit area (1.83 Q per 100 $m^2$). Further the parent plant 'Himalaya' from which 'Saksham' was derived produces 0.7% essential oil with 80% menthol and total biomass production from unit area is less than 'Saksham' (1.25 Q per 100 $m^2$) and more than 'Kalka'. Conclusively, 'Saksham' yields significantly more menthol per unit area compared to the high menthol variety 'Kalka' (CIMAP/HY-77) as well as the parent plant 'Himalaya' in addition to the best check variety 'Kosi' (Table 1) and hence, is a novel plant with most desirable trait of high menthol production.

TABLE 2

Additional description of 'Saksham' compared to the parent 'Himalaya' and high menthol yielding variety 'Kalka'.

| Sl. No. | Character | cv. *Kalka* | cv. *Himalaya* | cv. *Saksham* |
|---|---|---|---|---|
| 1. | Leaf:stem ratio | 1.0 | 1.5 | 1.5 |
| 2. | Stem | | | |
| | *color | Green (141C) Lower pigmented red purple (71B) | Green (143C) lower purplish (70A) | Green (143C) lower purplish (70A) |
| | *Stiffness | Hard | Hard | Hard |
| | *Thickness at 5th internode (mm) | 3.6 | 8.0 | 9.0 |
| 3. | Leaf | | | |
| | *Color | Green (139C) | Green (138B) | Green (138B) |
| | *Length (cm) | 6.7 | 6.2 | 8.0 |
| | *Width (cm) | 2.4 | 3.6 | 5.2 |
| | *Area ($cm^2$) | 8.7 | 15.1 | 15.6 |
| 4. | Petiole length (cm) | 1.2 | 1.5 | 2.2 |
| 5. | Flower color | Whitish | Pinkish white | Pinkish white (56C) |
| 6. | Flower length (mm) | 3.48 | 3.72 | 3.50 |
| 7. | Calyx color | Green (143B) With red purple streaks (71B) | Green (143C) | Green (143C) |
| 8. | Stigma color | White | White | Purplish white (76A) |
| 9. | Disease incidence to | | | |
| | *Rust | Resistant | Resistant | Resistant |
| | *Alternaria leaf blight | Resistant | Resistant | Resistant |
| | *Corynespora leaf spot | Tolerant | Tolerant | Tolerant |
| | *Powdery mildew | Susceptible | Tolerant | Tolerant |

Evidence of Uniformity and Stability

No variants of any kind (morphological or molecular) have been observed since 1997 (the year of development) and through yield trials in the following two years indicating the stability and uniformity of the genotype. Further, the comparative herbage, oil and ultimately menthol yields of 'Saksham' were significantly higher in comparison to the parent variety 'Himalaya', the high menthol yielding variety 'Kalka' (CIMAP/HY77), and best variety check 'Kosi' in different years and seasons. The traits of increased menthol content combined with higher essential oil and herbage yield is unprecedented and stable. In other words, the variety 'Saksham' has distinctive features from that of known plants and these distinctive features are very stable for repeated cultivation.

Statement of Distinction

The genotype 'Saksham' possessing the traits of increased menthol content combined with higher essential oil and herbage yield is unique and unprecedented not possessed by any known variety. The genotype has higher biomass and higher oil yield unit area in comparison to others. The total menthol yield of the new genotype is higher per unit area in comparison to other genotypes. Its genetic make up is distinct in terms of DNA profile.

Randomly Amplified Polymorphic DNA Analysis

The RAPD profiles of the plant 'Saksham' were unambiguously able to establish its distinct identity as completely different from the parent plant 'Himalaya' as well as the known released varieties. The plant of the present invention was developed by screening molecular variants among somaclones already differentiated as distinct, unique and novel at DNA level. The plant is having desirable morphological and economical traits in a rare unmatchable combination and is available only with us at CIMAP. No variation in the RAPD patterns was observed in the analysis of the micropropagated as well as field raised population in successive generations indicating the stability of the genotype. The 20 OPT primers (SEQ ID NOS.: 1–20) (OPT 01 to OPT 20) purchased from Operon Technologies, USA, with the sequence GGGCCACTCA, GGAGAGACTC, TCCACTCCTG, CACAGAGGGA, GGGTTTGGCA, CAAGGGCAGA, GGCAGGCTGT, AACGGCGACA, CACCCCTGAG, CCTTCGGAAG, TTCCCCGCGA, GGGTGTGTAG, AGGACTGCCA, AATGCCGCAG, GGATGCCACT, GGTGAACGCT, CCAACGTCGT, GATGCCAGAC, GTCCGTATGG, GACCAATGCC were used for the analysis to develop the unique fingerprint pattern.

Advantages

The advantages of the plant 'Saksham' are listed below:

1. The plant produces 22.6% higher menthol per unit area.
2. The essential oil yield per unit area is higher.
3. The herbage yield is more than 7% compare to best variety.
4. The new plant possesses better vegetative growth with high regenerability.

SEQUENCE LISTING

```
<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: OPT primer

<400> SEQUENCE: 1
```

-continued gggccactca 10

<210> SEQ ID NO 2
<211> LENGTH: 10
<212> TYPE: DNA
<213> ORGANISM: Artificial Sequence
<220> FEATURE:
<223> OTHER INFORMATION: OPT primer

<400> SEQUENCE: 2 ggagagactc 10

<210> SEQ ID NO 3
<211> LENGTH: 10
<212> TYPE: DNA
<213> ORGANISM: Artificial Sequence
<220> FEATURE:
<223> OTHER INFORMATION: OPT primer

<400> SEQUENCE: 3 tccactcctg 10

<210> SEQ ID NO 4
<211> LENGTH: 10
<212> TYPE: DNA
<213> ORGANISM: Artificial Sequence
<220> FEATURE:
<223> OTHER INFORMATION: OPT primer

<400> SEQUENCE: 4 cacagaggga 10

<210> SEQ ID NO 5
<211> LENGTH: 10
<212> TYPE: DNA
<213> ORGANISM: Artificial Sequence
<220> FEATURE:
<223> OTHER INFORMATION: OPT primer

<400> SEQUENCE: 5 gggtttggca 10

<210> SEQ ID NO 6
<211> LENGTH: 10
<212> TYPE: DNA
<213> ORGANISM: Artificial Sequence
<220> FEATURE:
<223> OTHER INFORMATION: OPT primer

<400> SEQUENCE: 6 caagggcaga 10

<210> SEQ ID NO 7
<211> LENGTH: 10
<212> TYPE: DNA
<213> ORGANISM: Artificial Sequence
<220> FEATURE:
<223> OTHER INFORMATION: OPT primer

<400> SEQUENCE: 7 ggcaggctgt 10

<210> SEQ ID NO 8
<211> LENGTH: 10
<212> TYPE: DNA

-continued

<213> ORGANISM: Artificial Sequence
<220> FEATURE:
<223> OTHER INFORMATION: OPT primer

<400> SEQUENCE: 8 aacggcgaca 10

<210> SEQ ID NO 9
<211> LENGTH: 10
<212> TYPE: DNA
<213> ORGANISM: Artificial Sequence
<220> FEATURE:
<223> OTHER INFORMATION: OPT primer

<400> SEQUENCE: 9 caccccctgag 10

<210> SEQ ID NO 10
<211> LENGTH: 10
<212> TYPE: DNA
<213> ORGANISM: Artificial Sequence
<220> FEATURE:
<223> OTHER INFORMATION: OPT primer

<400> SEQUENCE: 10 ccttcggaag 10

<210> SEQ ID NO 11
<211> LENGTH: 10
<212> TYPE: DNA
<213> ORGANISM: Artificial Sequence
<220> FEATURE:
<223> OTHER INFORMATION: OPT primer

<400> SEQUENCE: 11 ttccccgcga 10

<210> SEQ ID NO 12
<211> LENGTH: 10
<212> TYPE: DNA
<213> ORGANISM: Artificial Sequence
<220> FEATURE:
<223> OTHER INFORMATION: OPT primer

<400> SEQUENCE: 12 gggtgtgtag 10

<210> SEQ ID NO 13
<211> LENGTH: 10
<212> TYPE: DNA
<213> ORGANISM: Artificial Sequence
<220> FEATURE:
<223> OTHER INFORMATION: OPT primer

<400> SEQUENCE: 13 aggactgcca 10

<210> SEQ ID NO 14
<211> LENGTH: 10
<212> TYPE: DNA
<213> ORGANISM: Artificial Sequence
<220> FEATURE:
<223> OTHER INFORMATION: OPT primer

<400> SEQUENCE: 14

-continued aatgccgcag 10

<210> SEQ ID NO 15
<211> LENGTH: 10
<212> TYPE: DNA
<213> ORGANISM: Artificial Sequence
<220> FEATURE:
<223> OTHER INFORMATION: OPT primer

<400> SEQUENCE: 15 ggatgccact 10

<210> SEQ ID NO 16
<211> LENGTH: 10
<212> TYPE: DNA
<213> ORGANISM: Artificial Sequence
<220> FEATURE:
<223> OTHER INFORMATION: OPT primer

<400> SEQUENCE: 16 ggtgaacgct 10

<210> SEQ ID NO 17
<211> LENGTH: 10
<212> TYPE: DNA
<213> ORGANISM: Artificial Sequence
<220> FEATURE:
<223> OTHER INFORMATION: OPT primer

<400> SEQUENCE: 17 ccaacgtcgt 10

<210> SEQ ID NO 18
<211> LENGTH: 10
<212> TYPE: DNA
<213> ORGANISM: Artificial Sequence
<220> FEATURE:
<223> OTHER INFORMATION: OPT primer

<400> SEQUENCE: 18 gatgccagac 10

<210> SEQ ID NO 19
<211> LENGTH: 10
<212> TYPE: DNA
<213> ORGANISM: Artificial Sequence
<220> FEATURE:
<223> OTHER INFORMATION: OPT primer

<400> SEQUENCE: 19 gtccgtatgg 10

<210> SEQ ID NO 20
<211> LENGTH: 10
<212> TYPE: DNA
<213> ORGANISM: Artificial Sequence
<220> FEATURE:
<223> OTHER INFORMATION: OPT primer

<400> SEQUENCE: 20 gaccaatgcc 10

We claim:

1. A new and distinct cultivar of *Mentha arvensis* plant named 'Saksham' substantially as herein illustrated and described.

* * * * *

M1 M20